(12) United States Patent
Salvi

(10) Patent No.: US 7,283,235 B2
(45) Date of Patent: Oct. 16, 2007

(54) OPTICAL DEVICE AND INSPECTION MODULE

(75) Inventor: Aldo Salvi, La Chaux-de-Fonds (CH)

(73) Assignee: Ismeca Semiconductor Holding SA, La Chaux-de-Fonds (CH)

( * ) Notice: Subject to any disclaimer, the term of this patent is extended or adjusted under 35 U.S.C. 154(b) by 0 days.

(21) Appl. No.: 11/057,590

(22) Filed: Feb. 14, 2005

(65) Prior Publication Data

US 2005/0185181 A1    Aug. 25, 2005

Related U.S. Application Data

(63) Continuation of application No. PCT/CH2004/000074, filed on Feb. 9, 2004.

(30) Foreign Application Priority Data

Mar. 7, 2003    (CH) ..................................... 0365/03

(51) Int. Cl.
*G01B 11/30* (2006.01)
(52) U.S. Cl. ............... 356/394; 356/237.2; 250/559.08
(58) Field of Classification Search .. 356/237.1–237.6, 356/394; 250/559.08, 559.34, 223 R; 382/8, 382/145–146, 150–151
See application file for complete search history.

(56) References Cited

U.S. PATENT DOCUMENTS 5,909,285 A    6/1999   Beaty et al.
6,242,756 B1 *  6/2001   Toh et al. .............. 250/559.34
6,243,164 B1 *  6/2001   Baldwin et al. ............ 356/624
6,307,210 B1 * 10/2001   Suzuki et al. .......... 250/559.08
6,445,518 B1 *  9/2002   Lee ............................ 359/833
6,567,161 B1 *  5/2003   Lee .......................... 356/237.1
6,573,987 B2 *  6/2003   Shires ..................... 356/237.2
6,813,016 B2 * 11/2004   Quist ...................... 356/237.1

FOREIGN PATENT DOCUMENTS

| EP | 1 139 090 A2 | 10/2001 |
|----|--------------|---------|
| WO | WO 02/17357 A2 | 2/2002 |
| WO | WO 02/44651 A1 | 6/2002 |
| WO | WO 03/032252 A2 | 4/2003 |

\* cited by examiner

*Primary Examiner*—Sang H. Nguyen
(74) *Attorney, Agent, or Firm*—Pearne & Gordon LLP

(57) ABSTRACT

Optical device for representing a central image (10) of an object (1) and at least one lateral image (11, 12, 13, 14) of the same object (1), with the length of the real optical path of said central image (10) being different from the length of the real optical path of said at least one lateral image (11, 12, 13, 14) and the length of the apparent optical path of said central image (10) being equal to the length of the apparent optical path of said at least one lateral image (11, 12, 13, 14), and module for the optical inspection of objects comprising such an optical device and an optical system (7) allowing a central image (10) of the object (1) and at least one lateral image (11, 12, 13, 14) of this same object (1) to be captured simultaneously. The apparent optical paths of the central image (10) and of the lateral image (11, 12, 13, 14) being identical, these two images can be captured and correctly focussed simultaneously by a same viewing system (7).

17 Claims, 4 Drawing Sheets

OPTICAL DEVICE AND INSPECTION MODULE

REFERENCE DATA

This application is a continuation of PCT application PCT/CH2004/000074 (WO2004/079427) filed on Feb. 9, 2004, under priority of Swiss patent application 2003CH-0365 filed on Mar. 7, 2003, the contents whereof are hereby incorporated.

FIELD OF THE INVENTION

The present invention concerns an optical device and an inspection module comprising such a device. The present invention concerns in particular an optical device and an inspection module allowing an image from the lower side or upper side of an object and the image of at least one lateral side of the same object to be captured simultaneously, through a shooting device.

DESCRIPTION OF RELATED ART

Such modules are used for example for inspecting electronic components, for example leadless components (QFN, MLP, . . . ), dies or components with formed leads. They generally comprise a viewing system towards which are directed the image of the lower or upper side of a component to be inspected and the image of at least one of its lateral sides. The viewing system captures these images simultaneously for example for representing them together on a screen and/or for processing them digitally in order to detect possible anomalies of the component.

Certain inspection modules allow in particular the image of the lower (or upper) side 10 and the images of the four lateral sides 11, 12, 13, 14 of a same component 1 illustrated diagrammatically in FIG. 1 to be captured simultaneously, as so-called 5S (5 sides) inspection. FIG. 2 illustrates an example of representation of an electronic component by the viewing system of a 5S inspection device. The image of the component's lower side 10 is visible at the center of the representation, while the images of its four lateral sides 11, 12, 13, 14 are visible on the sides.

FIG. 3 illustrates diagrammatically the optical device of a prior art inspection module. The images of the lateral sides 12, 14 of the component 1 are directed towards the viewing system 7, for example the objective of a camera, by means of mirrors 2 placed on the sides of the component 1 to be inspected. For better readability, only two mirrors 2 are represented in FIG. 3. In the case of an optical device allowing a 5S inspection, the latter however comprises four mirrors, each mirror being placed opposite one of the four lateral sides of the component 1.

From FIG. 3 will clearly emerge that the length of the optical path A of the central image 10 is not equal to the length of the optical path c of the lateral images 12, 14. The length difference $\Delta l_o$ between these two paths is:

$$\Delta l_o = b + \frac{d}{2} + \frac{h}{2}.$$

Practically, this value often represents several millimeters, which is generally greater than the depth of focus of the objectives used by the viewing system 7, particularly in the case when very small components 1 are inspected, which requires strongly enlarging objectives. It is then difficult, or even impossible in certain cases, to have simultaneously a correctly focused central image 10 and correctly focused lateral images 11, 12, 13, 14. As at least one of these images is slightly blurred, there result measuring errors or a lack of precision in the inspection of the surface of the component 1.

It is thus an aim of the present invention to propose an optical device capable of avoiding the inconveniences of the prior art optical devices.

It is an aim of the present invention in particular to propose an optical device allowing a correctly focused and simultaneous representation of a central image of an object and of at least one lateral image of the same object, even for small objects.

It is another aim of the invention to propose an inspection module allowing the simultaneous visual inspection of the lower and/or upper side of a small-size component and of at least one of its lateral sides to be performed in optimal conditions.

BRIEF SUMMARY OF THE INVENTION

These aims are achieved by an optical device and by an inspection device having the characteristics of the corresponding independent claims, advantageous embodiments being further indicated by the dependent claims.

These aims are achieved in particular by an optical device for representing a central image of an object and at least one lateral image of the same object, with the length of the actual optical path of the central image being different from the length of the actual optical path of the lateral image and with the length of the apparent optical path of the central image being equal to the length of the apparent optical path of the lateral image, and by a module for the optical inspection of objects comprising such an optical device and an optical system allowing a central image of the object and at least a lateral image of this same object to be captured simultaneously.

According to the invention, since the apparent optical paths of the central image and of the lateral image are identical, these two images can be captured and correctly focused simultaneously by a single viewing system.

BRIEF DESCRIPTION OF THE DRAWINGS

The present invention will be better understood by means of the description of a preferred embodiment illustrated by the attached FIGS. 1 to 8, in which.

DETAILED DESCRIPTION OF THE INVENTION

Figure 1:
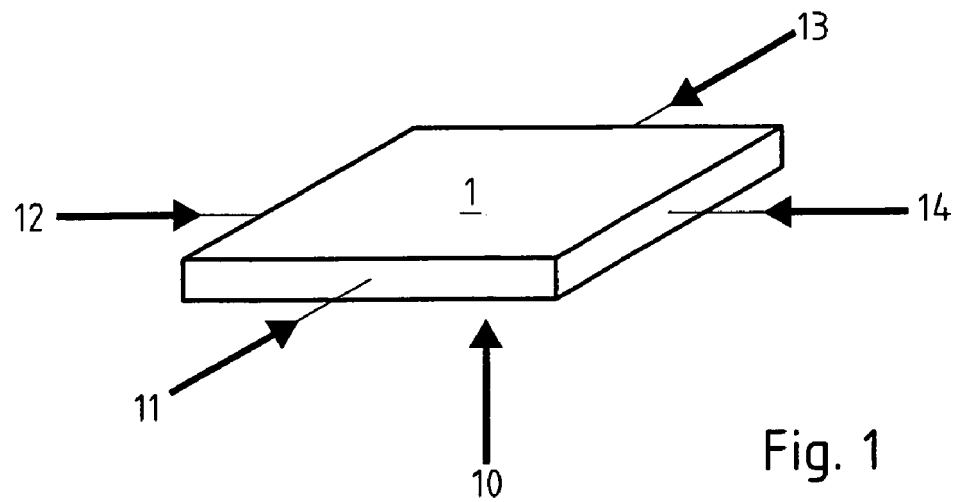
FIG. 1, previously discussed, illustrates diagrammatically the principle of a 5S inspection, FIG. 2, previously discussed, illustrates a representation of an electronic component by the viewing system of a 5S inspection device, FIG. 3, previously discussed, illustrates diagrammatically the operating principle of a prior art optical device.
Figure 2:
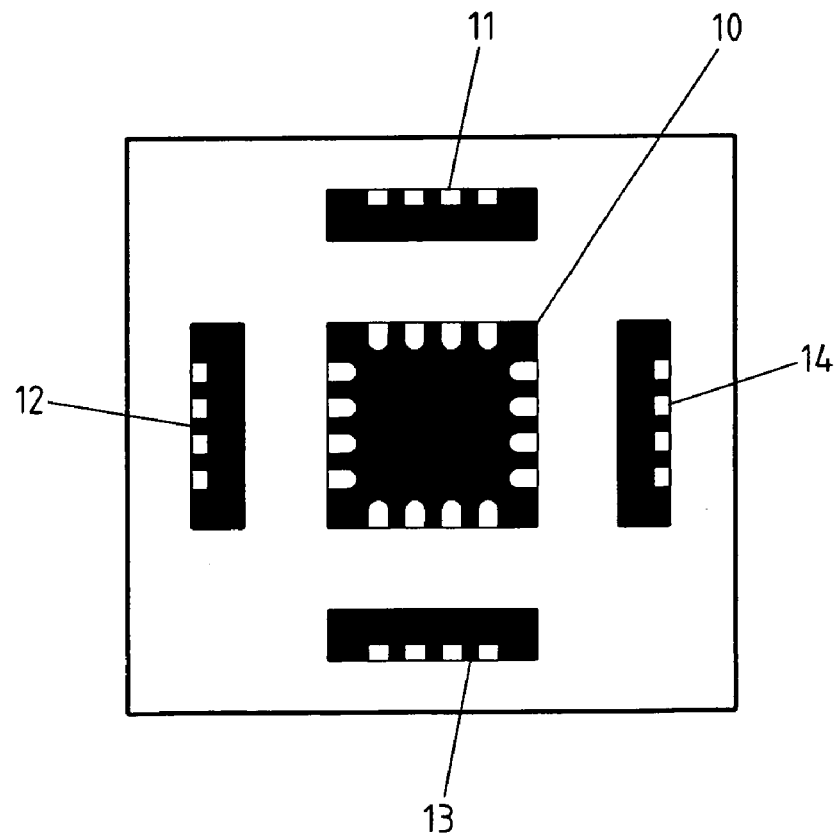
Figure 3:
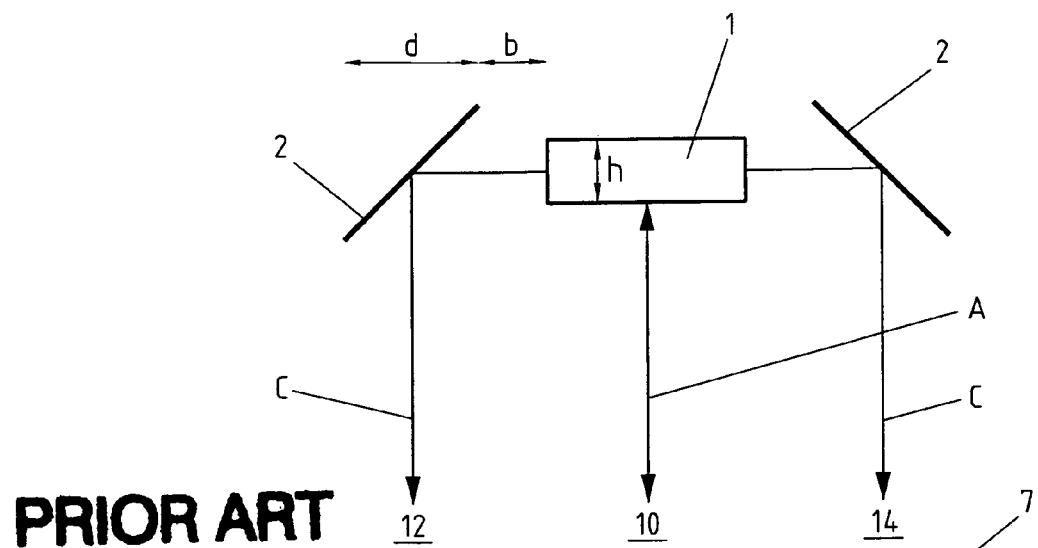
Figure 4:
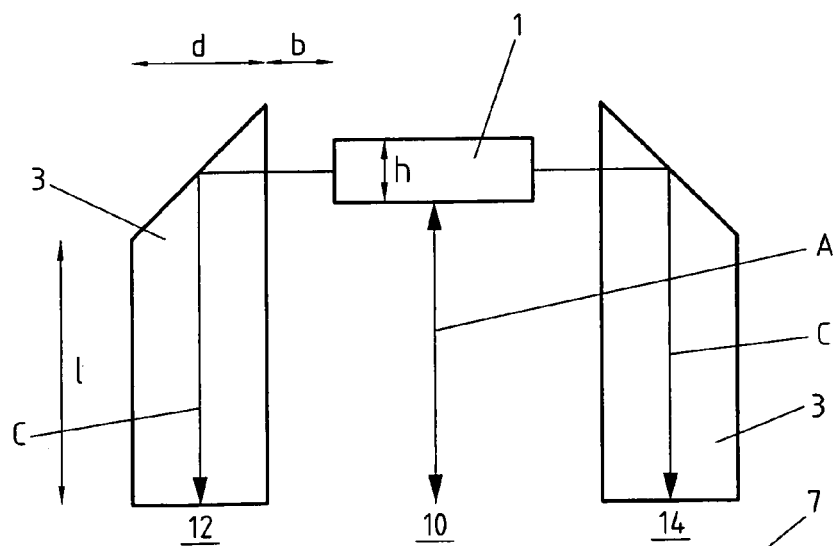
FIG. 4 illustrates diagrammatically the operating principle of the optical device according to a preferred embodiment of the invention.

FIG. 4 illustrates diagrammatically an optical device according to a preferred embodiment of the invention. It preferably comprises prisms 3 placed so as to leave sufficient space between them for inserting an object, for example an electronic component 1, to be inspected. For visibility reasons, only two prisms 3 are represented one opposite the other in FIG. 4. The number of prisms 3 is however determined according to need, for example according to the number of lateral sides of the object that are to be inspected simultaneously. In the case of a 5S inspection in particular, the optical device of the invention preferably comprises four prisms placed crosswise around the component to be inspected, according to the principle illustrated in FIG. 4. It is however also conceivable within the framework of the invention to imagine optical devices having three prisms placed in a triangle for inspecting an object having three lateral sides, etc.

The optical device of the invention is preferably associated to a viewing system 7, represented partially and diagrammatically in FIG. 4, allowing images returned by the optical device to be captured and possibly processed and/or represented. For this purpose, the viewing system 7 preferably comprises a shooting device, for example a camera, whose objective is placed in such a manner that it is capable of capturing the images returned by the optical device. It is also conceivable, in particular for reasons of space requirements, to orient the objective of the shooting device in another direction, for example perpendicularly to the exit direction of the images of the optical device, and to redirect the latter towards the shooting device, for example by means of a returning device not represented in FIG. 4 and comprising for example a prism or a mirror. The use of a returning device thus allows a greater liberty in placing the shooting device relative to the optical device, which is often desirable or even necessary, particularly when the space available, for example under the optical device, is limited.

The component 1 to be inspected is temporarily placed between the prisms 3, opposite the viewing system 7. It is preferably held in this position by its side opposite to the viewing system 7, for example by its upper side, by means of a component-holder (not represented), for example an aspiration nozzle of an electronic component conveyor.

The central image 10 of the component 1, for example the image of its lower side, is thus captured directly by the viewing system 7, whilst its lateral images 12, 14 are reflected and redirected towards the viewing system 7 through the prisms 3. The optical device of the invention thus preferably comprises a prism 3 for each lateral side to be inspected. In the case of an optical device allowing a 5S inspection, for example, the latter comprises four prisms 3 placed crosswise around the component, each prism 3 being opposite one of its lateral sides.

In the preferred embodiment illustrated by way of example in FIG. 4, the central image 10 of the component 1 is the image of its lower side which is captured directly by the viewing system 7 placed under the optical device. The prisms 3 are thus placed so as to redirect the images of its lateral sides 12, 14 also downwards, towards the viewing system 7. The one skilled in the art will however understand that it is perfectly conceivable within the framework of the invention to hold the component by its lower side and to place the viewing system opposite the component's upper side. The prisms are then preferably oriented so as to redirect the lateral images also upwards, so that the optical device can allow the simultaneous inspection of the component's upper side, which is then the central image, and of at least one of its lateral sides.

The prisms 3 are constituted of a translucent material having a refraction coefficient different from that of air. The length of the apparent optical path of the lateral images going through them is thus different from the length of the actual optical path of these images. According to the invention, as will also be explained further below, the dimensions l, d of the prisms 3 and/or their refraction coefficient are chosen so that the length of the apparent optical path of the lateral sides 12, 14 is equal to the length of the apparent optical path of the central image 10 despite their actual optical paths being of different lengths. As the central image 10 and the lateral images 12, 14 captured by the viewing system 7 all travel an apparent optical path of same length, they appear correctly focused for the same focal distance of the viewing system 7. They can thus all be represented correctly focused and simultaneously by the viewing system, thus allowing for example an optimal visual inspection of the component's surface.

Figure 5:
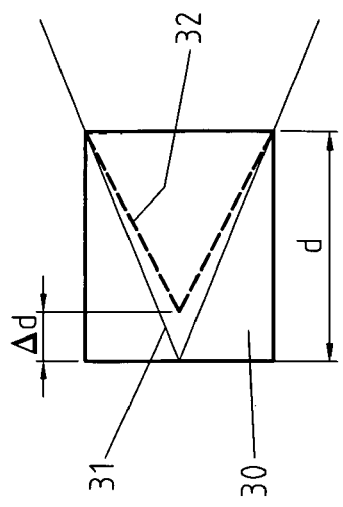
FIG. 5 illustrates the effects of a material having a refraction coefficient different from that of air on a light ray entering it.

The principle of the invention will be better understood by means of the theoretical reminder given hereafter and illustrated by FIG. 5: an object observed through an optical blade 30 with a refraction coefficient n and a width d appears closer than it actually is. The apparent optical path 32 of its image is thus reduced relative to the actual optical path 31. The continuous line in FIG. 5 represents the actual optical path 31, whilst the discontinued line represents the apparent optical path 32. The difference $\Delta d$ between the actual distance to the object and the apparent distance is calculated as follows:

$$\Delta d = d \cdot (n-1)/n.$$

According to the preferred embodiment of the invention illustrated by way of example in FIG. 4, the length differences of the optical paths as observed in the prior art optical devices are thus compensated by using prisms 3 for redirecting and forwarding the lateral images towards the viewing system 7. The dimensions d, l of the prisms 3 as well as the refraction coefficient n of the material used are chosen so that the length of the apparent optical path of the lateral images 12, 14 has the same length of the apparent optical path of the central image 10.

In the example of FIG. 4, no optical element is placed between the lower side of the component 1 and the viewing system 7. The central image is thus captured directly by the latter, without any other intermediary element but air, which has a refraction coefficient generally close to 1. The length of the apparent optical path of the central image 10 is thus identical to the length of its actual optical path A.

Under the effect of the prisms 3, the difference between the length of the actual optical path c of the lateral images 12, 14 and the length of their apparent optical path is however equal to:

$$\Delta l_p = (l+d) \cdot (n-1)/n.$$

The difference between the length of the actual optical path c of the lateral images 12, 14 and the length of the actual optical path A of the central image 10 is itself of:

$$\Delta l_o = b + d/2 + h/2,$$

where h is the height of the component 1.

In order to compensate this length difference of the actual optical paths c and A with the difference between the actual optical path c of the lateral images and their apparent optical path, the prisms 3 must be dimensioned to fulfill the equation:

$$\Delta l_o = \Delta l_p,$$

which equals:

$$b + d/2 + h/2 = (l+d) \cdot (n-1/n).$$

When this equation is fulfilled, the length of the apparent optical path of the lateral images 12, 14 is equal to the length of the apparent optical path of the central image 10. The focal distance of the viewing system 7 can thus be regulated so that the lateral images 12, 14 and the central image 10 are simultaneously correctly focused.

In practice, the height h of the component 1, the distance b between the component 1 and the prism 3 and the width d of the prism 3 are defined by mechanical and imagery conditions. The prism's length l is thus adjusted in order to obtain the equality indicated here above.

These dimensions are for example:

b=1 mm d=3.2 mm h=1 mm n=1.52 (BK7)

In this case, the prism's length must be of: l=5.9 mm.

In the preferred embodiment of the inventive device described here above by way of example, the prisms 3 are all identical and placed so that the distance between them and the corresponding lateral side of the component 1 to be inspected is the same for each. The one skilled in the art will however understand that it is possible, within the framework of the invention, to place each prism at a different distance from the lateral side whose image he must redirect. The dimensions l, d and/or the refraction coefficient n can then be different for each prism of the device in order to compensate the length differences between the actual optical paths of each image.

According to need, the prisms 3 can also be replaced or accompanied by other types of optical elements (not represented) allowing also the apparent length of the images' optical path to be modified. It is for example conceivable, within the framework of the invention, to compensate the length differences of the actual optical paths of the different images 10, 11, 12, 13, 14 by means of one or several optical conductors having for example each different dimensions and/or refraction coefficients, placed on the optical path of the lateral images and/or on the optical path of the central image.

According to a preferred embodiment, the optical device of the invention is integrated in an optical inspection module allowing for example electronic components with a side of 2 to 12 mm to be inspected. The one skilled in the art will however understand that it is conceivable, within the framework of the invention, to adapt the dimensions of the optical device when inspecting components having other dimensions, in particular when inspecting smaller components.

Figure 6:
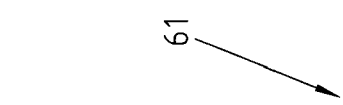
FIG. 6 represents an inspection module according to a preferred embodiment of the invention.

According to a preferred embodiment of the invention illustrated in cross-section in FIG. 6, the optical inspection module comprises:

1. an optical device according to the invention comprising for example four prisms 3, of which only two are represented in FIG. 6, placed crosswise to allow a 5S inspection of the components, 2. three lightings preferably configurable with a software: a coaxial lighting 50, a first annular lighting 51 and a second annular lighting 52, 3. a viewing system comprising a high-resolution digital camera 70, for example at least 1400×1050 pixels, preferably equipped with a zoom 71 allowing the visual field of the viewing system to be adapted to the components' size.

In its preferred embodiment, the optical module is adapted to being used on an electronic component processing line articulated for example around a circular conveyor 9 (partially represented). Such a processing line generally comprises a sequence of processing stations, for example testing, inspection and/or conditioning stations, placed around a central circular conveyor 9 carrying the components 1 from one processing station to the next by means of component-holders, for example aspiration nozzles 90, placed at its periphery. The movements of the circular conveyor 9 are indexed so as to present at each step a new electronic component to each processing station.

The processing line is preferably commanded and controlled by a control system (not represented) allowing in particular all the line's elements to be coordinated.

The optical module comprising the optical device of the invention is thus placed around the conveyor 9 of the processing line. It is preferably fastened onto a supporting plate 6 comprising fastening elements (not represented) allowing it to be fastened on a stationary plate 900 under the conveyor 9. The stationary plate 900 preferably has the same fastening elements (not represented) at each location provided for a processing station. The optical module can thus be integrated in a perfectly modular manner into the processing line.

When the optical module is placed under the conveyor 9, the optical device comprising the prisms 3 is placed in such a manner that at each step of the conveyor 9, an electronic component 1 finds itself precisely over its center, preferably at equal distance to each prism 3. During the conveyor's stopping time, the aspiration nozzle 90 holding the component 1 by its upper surface is lowered so that the component 1 finds itself inside the optical device, in the position illustrated in FIG. 6, and can thus be inspected by the viewing system 7.

For reasons of space requirements, the camera 70 is placed horizontally. Its shooting axis is thus horizontal. The central and lateral images coming out of the optical device of the invention are thus redirected in the axis of the shooting axis of the viewing system, for example by means of an additional prism 72, preferably unique.

Figure 7:
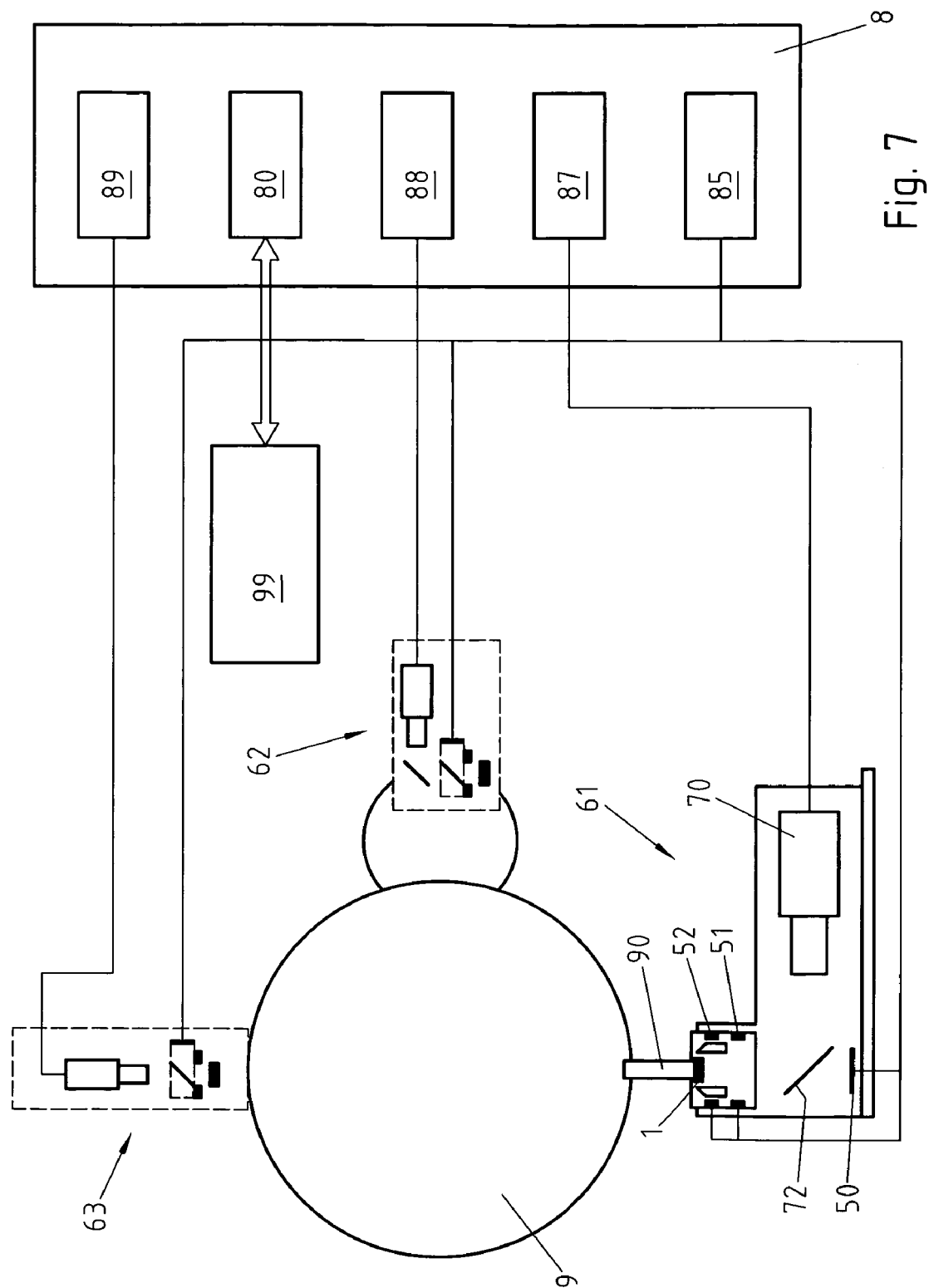
FIG. 7 represents an example of integration of an inspection module according to the invention to a complete inspection system on a component processing line.

With reference to FIG. 7, the optical module 61 of the invention is for example integrated into a component processing line articulated around a circular conveyor 9 and commanded by a vision control system 8, implemented at least partially for example on a personal computer or any other digital computer. The vision control system 8 preferably comprises an input/output card 80 allowing for example communication with the control system 99 of the conveyor 9 and thus ensuring an optimal coordination of these elements.

The vision control system 8 also preferably commands all the components of the optical module 61, in particular the lightings 50, 51, 52 and the shooting device 70. The lightings 50, 51, 52 of the optical module of the invention are for example configured and commanded by means of a light control module 85 that is part of the vision control system 8 and implemented on the personal computer, whilst the shooting device 70 is operated by an image capturing module 87 allowing for example the shooting to be triggered and the captured images to be processed.

The inspection, for example 5S, effected by means of the optical module 61 of the invention can be completed, on the component processing line, for example by two additional optical inspection modules, an on-the-plate inspection module 62 allowing the state of the components' upper surface to be controlled and an on-belt inspection module 63 capable of performing a last visual control of the components before or during their conditioning, for example in alveolar strips. Each of these inspection modules is preferably also operated by the vision control system 8 and their lighting is for example also controlled by the light control module 85. The inspection modules 62 and 63 also preferably each comprise a shooting device whose images are for example processed by image capturing modules 88 respectively 89 of the viewing control system 8.

According to a variant embodiment of the invention, the optical inspection module 61 of the invention comprises its own independent control system interacting with the vision control system 8 of the processing line through adapted input/output interfaces.

According to its preferred embodiment, the optical device of the invention is used for simultaneously inspecting the lower or upper side and at least one lateral side of electronic components. The dimensions of most electronic components and the dimensions of the devices for inspecting them are particularly well suited for correcting the optical path through the length of the prism 3, whose necessary length remains within acceptable dimensions. The one skilled in the art will however understand that the principle of the invention can be applied to other domains requiring for example the correctly focused and simultaneous representation by the same viewing system of several sides of a large-size object. Certain applications are however likely to require the use of prisms of impracticable or even unrealizable dimensions.

The inventive device is described here above within the framework of the inspection of electronic components. The one skilled in the art will however understand that the optical device of the invention can perfectly be used for simultaneously representing a central image and at least one lateral image of any other type of object.

The invention claimed is:

1. An optical device for representing a central image of an object and a lateral image of said object, said device comprising:
    a component for receiving images of the object, wherein the actual optical path length from the central image to the component is different than the actual optical path length of the lateral image to the component;
    a prism adapted for making an apparent optical path length of the lateral image to the component substantially equal to the actual optical path length of the central image of the component;
    at least one lateral lighting source for lighting said lateral image; and
    at least one distinct coaxial lighting source for lighting said central image.

2. The optical device of claim 1, with at least portions of the optical path of said central image and of the optical path of said lateral image having different refraction coefficients.

3. The optical device of claim 2, said lighting being software controlled.

4. The optical device of claim 1, with the refraction coefficient of said prism being greater than the refraction coefficient of air.

5. The optical device of claim 1, with the difference between the length of the real optical path of said lateral image and the length of the apparent optical path of said lateral image being generated by the optical properties of said prism.

6. The optical device of claim 1, said object being an electronic component.

7. Module for the optical inspection of objects, comprising an optical device according to claim 1 and an optical system allowing the central image of the object and the lateral image of said object to be captured simultaneously.

8. The module of claim 7, said optical system comprising an image capture device.

9. The module of claim 8, said optical system comprising said prism, another prism, or a mirror for redirecting one or both of said central image and said lateral image in the direction of said image capture device.

10. The module of claim 7, comprising a support allowing its integration into a processing line.

11. The module of claim 7, said objects being electronic components.

12. The optical device of claim 1, wherein said prism is further adapted to reflect said lateral image toward said component.

13. An optical device for representing a central image of an object and a lateral image of said object, said device comprising:
    a component for receiving images of the object, wherein the actual optical path length from the central image to the component is different than the actual optical path length of the lateral image to the component;
    a reflecting surface for reflecting the lateral image toward the component; and
    an optical path adjusting device adapted for making an apparent optical path length of the lateral image to the component substantially equal to the actual optical path length of the central image to the component.

14. The device of claim 13, further comprising at least one lateral lighting source for lighting said lateral image, and at least one distinct coaxial lighting source for lighting said central image.

15. The device of claim 13, wherein a surface of a triangular part of a prism is used as the reflecting surface and further wherein a rectangular part of said prism is used as said optical path adjusting device.

16. An optical device for representing a central image of an object and a lateral image of said object, said device comprising:
    a component for receiving images of the object, wherein the actual optical path length from the central image to the component is different than the actual optical path length of the lateral image to the component;
    a prism for adjusting an apparent optical path length of the lateral image to the component to be substantially equal to the actual optical path length of the central image to the component, said prism comprising:
        a triangular part for reflecting the lateral image toward the component; and
        a rectangular part, wherein most of said adjusting is performed in said rectangular part.

17. The device of claim 16, further comprising at least one lateral lighting source for lighting said lateral image, and at least one distinct coaxial lighting source for lighting said central image.

* * * * *